United States Patent
Banna et al.

(10) Patent No.: US 10,842,995 B2
(45) Date of Patent: *Nov. 24, 2020

(54) METHOD AND SYSTEM FOR USE OF HEARING PROSTHESIS FOR LINGUISTIC EVALUATION

(71) Applicant: Cochlear Limited, Macquarie University (AU)

(72) Inventors: Rami Banna, Paddington (AU); Alexander Case, Enmore (AU); Florent Hubert-Brierre, Meise (BE); Andrew Kendrick, Rosebery (AU)

(73) Assignee: COCHLEAR LIMITED, Macquarie University (AU)

( * ) Notice: Subject to any disclaimer, the term of this patent is extended or adjusted under 35 U.S.C. 154(b) by 317 days.

This patent is subject to a terminal disclaimer.

(21) Appl. No.: 15/784,723

(22) Filed: Oct. 16, 2017

(65) Prior Publication Data
US 2018/0036539 A1 Feb. 8, 2018

Related U.S. Application Data

(63) Continuation of application No. 13/892,747, filed on May 13, 2013, now Pat. No. 9,814,879.

(51) Int. Cl.
*A61N 1/36* (2006.01)
*H04R 25/00* (2006.01)

(52) U.S. Cl.
CPC ........ *A61N 1/36038* (2017.08); *H04R 25/407* (2013.01); *H04R 25/606* (2013.01)

(58) Field of Classification Search
CPC ........ A61N 1/36036–36038; H04R 25/00–75; H04R 2225/00–83; H04R 2460/00–17
See application file for complete search history.

(56) References Cited

U.S. PATENT DOCUMENTS

| | | | |
|---|---|---|---|
| 4,972,487 | A | 11/1990 | Mangold et al. |
| 5,824,022 | A | 10/1998 | Zilberman et al. |
| 7,027,606 | B2 | 4/2006 | D Agri |

(Continued)

FOREIGN PATENT DOCUMENTS

| | | |
|---|---|---|
| WO | 2001054456 A1 | 7/2001 |
| WO | 2007112737 A1 | 10/2007 |
| WO | 2012108128 A1 | 8/2012 |

*Primary Examiner* — Thaddeus B Cox
(74) *Attorney, Agent, or Firm* — Edell, Shapiro & Finnan, LLC (57) ABSTRACT

A method and system to help determine the extent to which a hearing prosthesis recipient is exposed to speech. The hearing prosthesis will log data regarding audio input, optimally in correspondence with times when the hearing prosthesis is in a stimulation-on mode in which the hearing prosthesis is set to stimulate a physiological system of the recipient in accordance with received audio input, so as to facilitate identification of speech to which the recipient is exposed. Further, as the hearing prosthesis itself receives the audio input, the hearing prosthesis may analyze the audio input to determine one or more linguistic characteristics of the audio input, such as a quantity of speech by the recipient and/or by others, and the hearing prosthesis may output data representing the determined one or more linguistic characteristics. Advantageously, the data may then be used to help facilitate rehabilitation of the recipient.

22 Claims, 5 Drawing Sheets

(56) References Cited

U.S. PATENT DOCUMENTS

| | | |
|---|---|---|
| 7,242,777 B2 | 7/2007 | Leenen et al. |
| 7,706,902 B2 | 4/2010 | Heubi et al. |
| 7,742,612 B2 | 6/2010 | Frohlich et al. |
| 7,933,419 B2 | 4/2011 | Roeck et al. |
| 7,986,790 B2 | 7/2011 | Zhang et al. |
| 8,077,892 B2 | 12/2011 | Dijkstra et al. |
| 8,085,961 B2 | 12/2011 | Aschoff et al. |
| 8,139,778 B2 | 3/2012 | Barthel et al. |
| 8,144,904 B2 | 3/2012 | Giese et al. |
| 2004/0190739 A1 | 9/2004 | Bachler et al. |
| 2007/0027676 A1 | 2/2007 | Chambers et al. |
| 2008/0260190 A1 | 10/2008 | Kidmose |
| 2009/0154741 A1 | 6/2009 | Woods et al. |
| 2010/0104122 A1 | 4/2010 | Waldmann |
| 2011/0093039 A1 | 4/2011 | Van Den Heuvel |
| 2011/0235835 A1 | 9/2011 | Buelow et al. |
| 2012/0020505 A1* | 1/2012 | Yamada ............... G10L 25/48 381/313 |
| 2012/0128186 A1* | 5/2012 | Endo .................. H04R 25/407 381/313 |
| 2012/0215532 A1 | 8/2012 | Foo et al. |
| 2013/0144622 A1* | 6/2013 | Yamada ............... G10L 25/48 704/248 |

* cited by examiner

METHOD AND SYSTEM FOR USE OF HEARING PROSTHESIS FOR LINGUISTIC EVALUATION

CROSS-REFERENCE TO RELATED APPLICATIONS

This application is a continuation of U.S. patent application Ser. No. 13/892,747, entitled "Method and System for Use of Hearing Prosthesis for Linguistic Evaluation," filed on May 13, 2013, now U.S. Pat. No. 9,814,879. The entire contents of which is incorporated herein by reference herein.

BACKGROUND

Unless otherwise indicated herein, the information described in this section is not prior art to the claims and is not admitted to be prior art by inclusion in this section.

Various types of hearing prostheses provide people with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

People with some forms of conductive hearing loss may benefit from hearing prostheses such as hearing aids or vibration-based hearing devices. A hearing aid, for instance, typically includes a small microphone to receive sound, an amplifier to amplify certain portions of the detected sound, and a small speaker to transmit the amplified sounds into the person's ear. A vibration-based hearing device, on the other hand, typically includes a small microphone to receive sound and a vibration mechanism to apply vibrations corresponding to the detected sound so as to cause vibrations in the person's inner ear. Examples of vibration-based hearing devices include bone anchored devices that transmit vibrations via the skull and acoustic cochlear stimulation devices that transmit vibrations more directly to the inner ear.

Further, people with certain forms of sensorineural hearing loss may benefit from hearing prostheses such as cochlear implants and/or auditory brainstem implants. Cochlear implants, for example, include a microphone to receive sound, a processor to convert the sound to a series of electrical stimulation signals, and an array of electrodes to deliver the stimulation signals to the implant recipient's cochlea so as to help the recipient perceive sound. Auditory brainstem implants use technology similar to cochlear implants, but instead of applying electrical stimulation to a person's cochlea, they apply electrical stimulation directly to a person's brain stem, bypassing the cochlea altogether, still helping the recipient perceive sound.

In addition, some people may benefit from hearing prostheses that combine one or more characteristics of the acoustic hearing aids, vibration-based hearing devices, cochlear implants, and auditory brainstem implants to enable the person to perceive sound.

SUMMARY

A person who suffers from hearing loss may also have difficulty speaking and appreciating speech by others, including in some cases developing language skills in the first place. When such a person receives a hearing prosthesis to help them better perceive sounds, it may therefore be important for the person to be exposed to a sufficient extent of speech (including both speech production and speech reception) so that the person can begin to improve their own speaking and to better appreciate speech by others. For example, once a person receives a hearing prosthesis, it may be important for the person to produce a sufficient quantity of speech themselves and to receive a sufficient quantity of speech from others, such as by engaging in a sufficient extent of speech interaction (e.g., conversation) with others. Further, it may be important for the speech exposure to be of sufficient quality and varying complexity, including for instance a sufficient number of clear words, sentences, and the like.

This may be the case especially for recipients of cochlear implants and other such prostheses that do not merely amplify received sounds but provide the recipient with other forms of physiological stimulation to help them perceive the received sounds. Exposing such a recipient to a good amount of speech (both received and produced by the recipient) may help the recipient begin to better correlate those physiological stimulations with the received sounds and thus improve the recipient's speech and appreciation of speech.

By the same token, knowing the extent to which a hearing prosthesis recipient is exposed to speech may help a clinician such as a speech therapist, teacher, or parent develop appropriate therapy to help rehabilitate the recipient. For example, given knowledge that the recipient is not speaking very often, is not being exposed to much speech of others, or is not engaging in sufficient conversation, a clinician may help the recipient to speak more often or may arrange for friends and family members of the recipient to speak with the recipient more often. As another example, given knowledge that the recipient is being exposed to a large amount of speech together with background noise such as television or music, a clinician may advise turning off the background noise sources to help improve the recipient's speech exposure. And as still another example, given knowledge of certain characteristics of the recipient's speech or of other speech in the recipient's environment, a clinician may develop strategies (e.g., activities or the like) to help the recipient engage in and be exposed to other forms of speech, to further rehabilitate the recipient.

Disclosed herein are methods and corresponding systems to help determine the extent to which a hearing prosthesis recipient is exposed to speech, including for instance the recipient's own speech, speech by others in the recipient's environment, and speech interaction between the recipient and others. The disclosed methods leverage the fact that, as the hearing prosthesis is in use by the recipient, the prosthesis itself receives audio input that represents the audio environment of the recipient including speech in that environment.

In accordance with the disclosure, the hearing prosthesis will log data regarding that received audio input, optimally in correspondence with times when the hearing prosthesis is set to stimulate a physiological system of the recipient in accordance with received audio input, so as to facilitate identification of speech to which the recipient is exposed. Further, as the hearing prosthesis itself receives the audio input, the hearing prosthesis may analyze the audio input to determine one or more linguistic characteristics of the audio input, such as a quantity of speech by the recipient and/or by others, and the hearing prosthesis may output data representing the determined one or more linguistic characteristics. Advantageously, the data may then be used to help facilitate rehabilitation of the recipient as discussed above.

Accordingly, in one respect, disclosed is a method that can be implemented by a recipient's hearing prosthesis such as one of those described above for instance. In accordance with the method, the hearing prosthesis receives audio input representing an audio environment of the recipient, and the hearing prosthesis is operable to stimulate a physiological system of the recipient in accordance with that received audio input. Further, the hearing prosthesis determines, based on that same received audio input, one or more linguistic characteristics of the audio environment, and the hearing prosthesis generates and outputs data representing the one or more determined linguistic characteristics.

In practice, such a hearing prosthesis may have a stimulation mode that switches between a stimulation-on mode in which the hearing prosthesis is set to stimulate the physiological system of the recipient in accordance with received audio input (e.g., to the extent the received audio input would result lead to such stimulation) and a stimulation-off mode in which the hearing prosthesis is set to not stimulate the physiological system of the recipient in accordance with the received audio input. (For instance, a cochlear implant may have a coil that may be on to set the implant in a stimulation-on mode or off to set the implant in a stimulation-off mode.) In that case, the act of generating the data representing the determined one or more linguistic characteristics may additionally involve basing the data at least in part on the stimulation mode of the hearing prosthesis. For instance, the hearing prosthesis may include in the data indicia of times when the hearing prosthesis was in the stimulation-on mode, such as indicia that indicate which determined linguistic characteristics correspond with those times of stimulation. Or the hearing device may limit the linguistic characteristic data to be with respect to just audio input that resulted in stimulation of the recipient's physiological system.

In another respect, disclosed is a method that can be similarly implemented by a recipient's hearing prosthesis. In accordance with this method, the hearing prosthesis receives audio input, and the hearing prosthesis is operable to stimulate a physiological system of the recipient in accordance with the received audio input. Further, at times while receiving the audio input, the hearing prosthesis is in a stimulation-on mode in which the hearing prosthesis is set to stimulate the physiological system of the recipient in accordance with the received audio input and at other times while receiving the audio input the hearing prosthesis is in a stimulation-off mode in which the hearing prosthesis is set to not stimulate the physiological system of the recipient in accordance with the received audio input. Pursuant to the method, the hearing prosthesis logs data representing the received audio input in correspondence with only the times when the hearing prosthesis is in the stimulation-on mode. Thus, the hearing prosthesis may limit the logging to be with respect to the just the audio input received when the hearing prosthesis was set to stimulate the recipient's physiological system in accordance with the audio input.

In still another respect, disclosed is a method that can be implemented by a hearing assistance device that is worn by or at least partially implanted into a human recipient. In accordance with this method, the hearing assistance device receives audio input representing an audio environment of the recipient, and the hearing assistance device is operable to stimulate a physiological system of the recipient in accordance with the received audio input. Further, the hearing assistance device records data representing the received audio input and specifying times when the hearing assistance device was operating in a stimulation-on mode in which the hearing assistance device was set to stimulate the physiological system of the recipient in accordance with the received audio input. Further, the method includes determining based on the recorded data one or more linguistic characteristics of the audio environment, and providing output that represents one or more determined linguistic characteristics.

In yet another respect, disclosed is a hearing assistance device (e.g., a hearing prosthesis such as any of those noted above) configured to be worn by or at least partially implanted in a human recipient and to stimulate a physiological system of the recipient, such as one of the hearing prostheses discussed above for instance. The disclosed device includes one or more microphones for receiving audio input representing an audio environment of the recipient, and the device is configured to stimulate the physiological system of the recipient in accordance with that received audio input. Further, the device is configured to (i) determine, based on the received audio input, one or more linguistic characteristics of the audio environment, (ii) generate data representing the one or more determined linguistic characteristics and (iii) output the data for evaluation. For instance, the device may include a processing unit, data storage, and program instructions stored in the data storage and executable by the processing unit to carry out the determining, generating, and outputting functions.

And in yet another respect, disclosed is a hearing instrument (e.g., a hearing prosthesis such as any of those discussed above) including one or more microphone inputs, one or more stimulus outputs, and a processing unit for receiving audio input from the one or more microphone inputs, generating stimulation signals, and providing the stimulation signals to the one or more stimulation outputs, so as to stimulate a physiological system of a recipient of the hearing instrument. The processing unit is then further configured to log data regarding operation of the hearing instrument and regarding an environment of a recipient, in correspondence with data indicating when the hearing instrument is set to provide the stimulation and when the hearing instrument is not set to provide the stimulation.

These as well as other aspects, advantages, and alternatives will become apparent to those of ordinary skill in the art by reading the following detailed description, with reference where appropriate to the accompanying drawings. Further, it should be understood that the description throughout by this document, including in this summary section, is provided by way of example only and therefore should not be viewed as limiting.

DETAILED DESCRIPTION

Referring to the drawings, as noted above, FIG. 1 is a simplified block diagram of an example hearing prosthesis 12 operable in accordance with the present disclosure. As shown, the example hearing prosthesis 12 generally includes one or more microphones (microphone inputs) 14 for receiving audio input representing an audio environment of the prosthesis recipient, a processing unit 16 having a translation module 18 for translating a representation of the received audio input into stimulation signals, and stimulation means (one or more stimulation outputs) for stimulating the physiological system of the recipient in accordance with the stimulation signals and thus in accordance with the received audio input.

Figure 1:
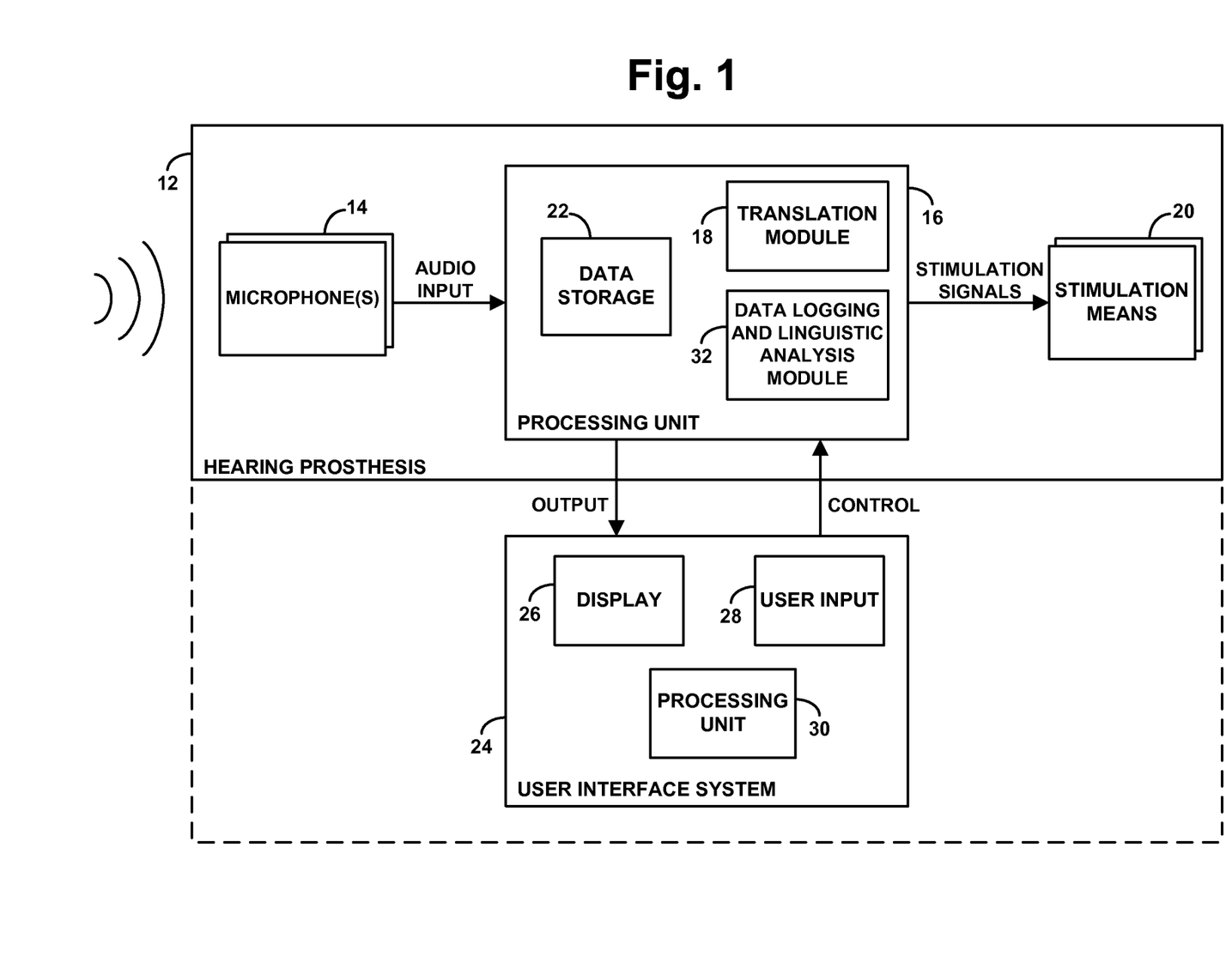
FIG. 1 is a simplified block diagram of an example hearing prosthesis.

This example hearing prosthesis may represent any of various types of hearing prosthesis, including but not limited to those discussed above, and the components shown may accordingly take various forms. By way of example, if the hearing prosthesis is a hearing aid, the translation module 18 may include an amplifier that amplifies the received audio input, and the stimulation means 20 may include a speaker arranged to deliver the amplified audio into the recipient's ear. As another example, if the hearing prosthesis is a vibration-based hearing device, the translation module 18 may function to generate electrical stimulation signals corresponding with the received audio input, and the stimulation means 20 may include a transducer that delivers vibrations to the recipient in accordance with those electrical stimulation signals. And as yet another example, if the hearing prosthesis is a cochlear implant, the translation module 18 may similarly generate electrical signals corresponding with the received audio input, and the stimulation means 20 may include an array of electrodes that deliver the stimulation signals to the recipient's cochlea. Other examples are possible as well.

In practice, the processing unit 16 may be arranged to operate on a digitized representation of the received audio input as established by analog-to-digital conversion circuitry in the processing unit, microphone(s) or one or more other components of the prosthesis. As such, the processing unit 16 may include data storage (e.g., magnetic, optical or flash storage) 22 for holding a digital bit stream representing the received audio and for holding associated data. Further, the processing unit 16 may include a digital signal processor, and the translation module 18 may be a function of the digital signal processor, arranged to analyze the digitized audio and to produce corresponding stimulation signals or associated output. Alternatively or additionally, the processing unit may include one or more general purpose processors (e.g., microprocessors), and the translation module 18 may include a set of program instructions stored in the data storage 22 and executable by the processor(s) to analyze the digitized audio and to produce the corresponding stimulation signals or associated output.

Further, the processing unit 16 may control and/or track the extent to which the hearing prosthesis stimulates the physiological system of the recipient. For instance, as noted above, the prosthesis may have a stimulation mode that can be switched between a stimulation-on mode and a stimulation-off mode. In the stimulation-on mode, the prosthesis would be set to stimulate the physiological system of the recipient in accordance with audio input being received by the prosthesis, such as by providing corresponding stimulation signals when the audio input is of sufficient amplitude and of particular frequency and to not provide stimulation signals if the audio input is threshold low amplitude or is of some other frequency. And in the stimulation-off mode, the prosthesis would be set to not stimulate the physiological system of the recipient in accordance with the audio input being received by the prosthesis, regardless of the amplitude and frequency of the audio input.

The processing unit may switch between these stimulation modes in accordance with user input or may determine when a user has switched the hearing prosthesis between these stimulation modes. For instance, the processing unit may receive user input directing the hearing prosthesis to switch between stimulation-on mode and stimulation-off mode, and the processing unit may responsively set the stimulation mode accordingly and make note of the current stimulation mode. Alternatively, a user may change the stimulation mode of the prosthesis (such as by switching between a coil-on mode and coil-off mode), and the processing unit may make note of that change in stimulation mode. Further, the processing unit may switch the prosthesis between stimulation-on mode and stimulation-off mode from time to time based on a programmed schedule or other trigger events and may similarly make note of the current stimulation mode.

As further shown, the example hearing prosthesis 12 includes or is coupled with a user interface system 24 through which the recipient or others (e.g., a clinician) may control operation of the prosthesis and view various settings and other output of the prosthesis. In practice, for instance, the user interface system 24 may include one or more components internal to or otherwise integrated with the prosthesis. Further, the user interface system 24 may include one or more components external to the prosthesis, and the prosthesis may include a communication interface arranged to communicate with those components through a wireless and/or wired link of any type now known or later developed.

In a representative arrangement, the user interface system 22 may include one or more user interface components that enable a user to interact with the hearing prosthesis. As shown by way of example, the user interface components may include a display screen 26 and/or one or more input mechanisms 28 such as a touch-sensitive display surface, a keypad, individual buttons, or the like. These user interface components may communicate with the processing unit 16 of the hearing prosthesis in much the same way that conventional user interface components interact with the host processor of a personal computer. Alternatively, the user interface system 24 may include one or more standalone computing devices such as a personal computer, mobile phone, tablet, handheld remote control, or the like, and may further include its own processing unit 30 that interacts with the hearing prosthesis and may be arranged to carry out various other functions.

In practice, user interface system 24 may enable the recipient to control the stimulation mode of the hearing prosthesis, such as to turn stimulation functionality on, and off. For instance, at times when the recipient does not wish to have the prosthesis stimulate the recipient's physiological system in accordance with received audio input, the recipient may engage a button or other input mechanism of the user interface system 24 to cause processing unit 16 to set the prosthesis in the stimulation-off mode. And at times when the recipient wishes to have the prosthesis stimulate the recipient's physiological system in accordance with the received audio input, the recipient may engage a similar mechanism to cause the processing unit 16 to set the prosthesis in the stimulation-on mode. Further, the user interface system 24 may enable the recipient or others to program the processing unit 16 of the prosthesis so as to schedule automatic switching of the prosthesis between the stimulation-on mode and the stimulation-off mode.

In accordance with the present disclosure, as noted above, the example hearing prosthesis 12 will additionally function to log and output data regarding the received audio input. In particular, the hearing prosthesis may analyze the received audio input so as to determine one or more linguistic characteristics in the recipient's audio environment and may output data representing the determined one or more linguistic characteristics. Further, the hearing prosthesis may use its stimulation mode as a basis to generate this data, such as by determining and logging linguistic characteristics just with respect to the audio input received while the hearing prosthesis is in the stimulation-on mode, or by separately recording (i) linguistic characteristics in the audio input received at times when the hearing prosthesis was in the stimulation-on and (ii) linguistic characteristics in the audio input received at times when the hearing prosthesis was in the stimulation-off mode.

The hearing prosthesis may then output it logged data from time to time for external analysis, such as for external determination and reporting of linguistic characteristics in the recipient's audio environment. For instance, the user interface system 24 may periodically poll the hearing prosthesis to obtain from the prosthesis the latest linguistic characteristics logged by the prosthesis, such as the latest logged linguistic characteristics corresponding with stimulation-on mode and the latest logged linguistic characteristics corresponding with stimulation-off mode. And the user interface system 24 may process that data and provide a graphical user interface that depicts a comparison of the logged linguistic characteristics (possibly per stimulation mode) over time.

Notably, the audio input that forms the basis for this analysis is the same audio input that the hearing prosthesis is arranged to receive and use as a basis to stimulate the physiological system of the recipient when the prosthesis is in the stimulation-on mode. Thus, as the hearing prosthesis receives audio input, the hearing prosthesis may not only translate that audio input into stimulation signals to stimulate the recipient's physiological system if the hearing prosthesis is in the stimulation-on mode but may also log data regarding the same received audio output, such as data regarding linguistic characteristics in the audio input in correlation with the stimulation mode. Further, even at times when the hearing prosthesis is receiving audio input but is not stimulating the recipient's physiological system (e.g., because stimulation is turned off or because the audio input amplitude or frequency is such that the prosthesis is set to not provide stimulation), the hearing prosthesis may still log data regarding that received audio input, such as linguistic characteristics in correlation with the stimulation mode. Any or all of this data may then be clinically relevant and useful in developing therapy and training (e.g., remediation) for the recipient.

As shown in FIG. 1, the processing unit 16 of the example hearing prosthesis 12 includes a data logging and linguistic analysis (DLLA) module 32 for carrying out some or all of these added functions. This DLLA module 32 may be integrated in whole or in part with the translation module 18, such as by making use of some of the same components of the hearing prosthesis as the translation module 18. Further, as with the translation module, this DLLA module may be provided in various forms. For instance, the DLLA module may be provided as a function of a digital signal processor, or as a set of program instructions stored in data storage and executable by one or more processors to carry out the data logging and linguistic analysis functions.

In practice, as the processing unit 16 receives audio input representing the audio environment of the recipient, the processing unit module may evaluate the audio input in real-time so as to determine one or more linguistic characteristics in the audio input.

The "linguistic characteristics" explored here are characteristics specifically related to language production and receipt, and therefore may or may not include more general audio characteristics such as amplitude, frequency, or the like. Examples of linguistic characteristics include, among others, (1) a measure of proportion of time spent by the recipient speaking, (2) a measure of proportion of time spent by the recipient receiving speech from others, (3) a measure of quantity of words spoken by the recipient, (4) a measure of quantity of sentences spoken by the recipient, (5) a measure of quantity of words spoken by one or more people other than the recipient, (6) a measure of quantity of sentences spoken by one or more people other than the recipient, (7) a measure of quantity of conversational turns by the recipient, (8) a measure of length of utterances by the recipient or by others, (9) a measure of quantity of phonetic features produced by the recipient, such as voiced vs unvoiced speech sounds, vowels versus consonants, or a more specific breakdown of consonant articulation such as plosives, affricatives, fricatives, sibilants, nasal, flap, tap, approximant, lateral, trill, and so forth, including for instance a measure of rate of syllabic or other speech production and/or a measure of phoneme variations created, (10) a measure of quality of speech exposure, such as presentation level and signal to noise ratio of the speech, (11) a measure of words spoken by adult versus words spoken by children, (12) a measure of quantity of conversations engaged in or initiated by the recipient, and (13) indications of whether the speech is shouted or conversational.

The processing unit may apply various well known audio analysis techniques, or other techniques now known or later developed, to determine the one or more linguistic characteristics in the audio input and may do so in real-time (e.g., continually or periodically as the hearing prosthesis receives the audio input).

For example, the processing unit may apply various well known trainable classifier techniques, such as neural networks, Gaussian Mixture models, Hidden Markov models, and tree classifiers. These techniques can be trained to recognize particular linguistic characteristics such as some of those noted above. For instance, a tree classifier can be used to determine the presence of speech in audio input. Further, various ones of these techniques can be trained to recognize segments or quiet spaces between words, and to recognize the difference between male and female voices. Moreover, these techniques could be scaled in order of complexity based on the extent of available computation power.

Implementation of a classifier may require several stages of processing. In a two-stage classifier, for instance, the first stage is used to extract information from a raw signal representing the received audio input provided by the one or more microphones. This information can be anything from the raw audio signal itself, to specific features of the audio signal ("feature extraction"), such as pitch, modulation depth etc. The second stage then uses this information to identify one or more probability estimates for a current class at issue.

In order for the second stage of this technique to work, it should be trained. Training involves, by way of example, collecting a pre-recorded set of example outputs ("training data") from the system to be classified, representing what engineers or others agree is a highest probability classification from a closed set of possible classes to be classified, such as audio of music or speech recorded through the prosthesis microphones. To train the second stage, this training data is then processed by the first stage feature extraction methods, and these first stage features are noted and matched to the agreed class. Through this design process, a pattern will ultimately be evident among all the feature values versus the agreed class collected. For example, all of the speech samples might have a modulation depth above 0.5, while all noise signals might be below 0.2. Well-known algorithms may then be applied to help sort this data and to decide how best to implement the second stage classifier using the feature extraction and training data available. For example, in a tree classifier, a decision tree may be used to implement an efficient method for the second stage. Nodes of the tree may thus have values such as "is modulation depth <0.5" as conditions for which direction to branch. And each path may end at a highest probability class decision (such as a classification as music, speech, etc.)

In applying such a technique to identify linguistic characteristics in the received audio input, the training data may for example contain spoken words and sentences, by male and female speakers of various ages, and perhaps speech specifically by the recipient. Further, the feature extraction stage may contain voiced and unvoiced speech segment detectors, and perhaps a fast moving level measure to track the time between gaps in sentences. A two-stage classifier could then be trained to recognize when a sentence had been spoken, and to distinguish other sounds as not being a sentence.

As another example, the processing unit may apply threshold detectors, such as to detect volume and energy levels in the received audio input, and to detect segments that indicate spaces between words, and perhaps to thereby detect the presence of words and sentences. Similar to the first stage of a classifier as discussed above, for instance, a set of signal features could be used to extract information from the audio input signal, and the processing unit may forego applying the second stage for classification. For example, the processing unit may detect threshold modulation depth in the audio input as an indication of the presence of speech, as speech may have modulation greater than other signals carrying little information (such as noise). Further, the processing unit may detect threshold root mean squared (RMS) signal level as a measure of gaps between sentences, to facilitate determining a quantity of sentences spoken.

By setting an appropriate threshold or thresholds for each of various signal features, the processing unit may thereby detect particular linguistic features. For example, if the modulation depth is greater than 0.5 and the RMS level is above 60 dB SPL, the processing unit may programmatically conclude that speech is present. Alternatively if the modulation depth is below 0.5 and the RMS level is below 50 dB SPL, the processing unit may determine that no speech is present. Further, by counting the length and difference between speech and non-speech segments, the processing unit may determine the number of sentences spoken.

As still another example, the processing unit may apply various well known speech recognition techniques to detect the extent of speech in the audio input. Those techniques may require significant computational power and may or may not be suitable for real-time analysis by prosthesis processing units without the assistance of an external processing unit for instance. However, continued developments in signaling processing technology and speech recognition algorithms may make actual speech recognition, including speaker recognition, more suitable for implementation by the processing unit of a hearing prosthesis.

Further, in terms of determining whether identified speech is speech of the recipient or speech of another person in the recipient's environment, the processing unit may take various factors into consideration. For instance, the processing unit may take into account loudness and frequency range of the speech, possibly by way of comparison with test samples of the recipient's own voice. In addition, if the prosthesis has multiple microphones for receiving the audio input and the processing unit receives separate audio input from each microphone, the processing unit may use those separate inputs to differentiate between (i) the recipient's speech as may be picked up by a microphone positioned to best pick up speech coming from the recipient and (ii) others' speech as may be picked up by a microphone positioned to best pick up speech directed at the recipient.

Moreover, to facilitate carrying out this analysis in real-time, the processing unit may limit its analysis to identify key parameters as proxies for more complex linguistic characteristics or may generally estimate various ones of the linguistic characteristics rather than striving to determine them exactly. For instance, rather than working to determine an exact count of words spoken by the recipient or spoke by others in the recipient's environment, the processing unit may determine an approximate count. Such an approximation may be clinically relevant, as it may facilitate general comparisons between extents of speech to which the recipient is exposed. For example, if the processing unit determines that the recipient is exposed to approximately 400 words one day and approximately 600 words the next day, that 50% estimated increase may be key to evaluating the recipient's speech exposure.

Optimally, as the processing unit receives the audio input, the processing unit may record various associated data in data storage 22. Further, the processing unit may output the data in real-time or at some later time to the user interface system 24.

By way of example, as the processing unit determines the one or more linguistic characteristics of the recipient's audio environment, the processing unit may record those characteristics in correspondence with indications of whether the hearing prosthesis is in the stimulation-on mode or is rather in the stimulation-off mode. For instance, the processing unit may keep track over time of the rate or number of words, sentences, or the like, in the audio input at times when the prosthesis is in the stimulation-on mode and may separately keep track over time of the rate or number of words, sentences, or the like, in the audio input at times when the prosthesis is in the stimulation-off mode. And the processing unit may output data representing these metrics, possibly in real-time as the processing unit generates the metrics. For instance, as noted above, the user interface system 24 may periodically poll the prosthesis for such metrics and may receive and timestamp the metrics, to facilitate determining and presenting changes in the metrics over time. Alternatively, the processing unit may push the data periodically to the user interface system or otherwise output the data.

Alternatively, the processing unit may limit its determination and logging of linguistic characteristics to be just with respect to audio input that the prosthesis receives at times when the hearing prosthesis is in the stimulation-on mode. For instance, the processing may track the linguistic characteristics just at times when the prosthesis is in the stimulation-on mode, and not at times when the prosthesis is in the stimulation off mode. And the processing unit may output data representing the determined linguistic characteristics, possibly in real-time as the processing unit determines the linguistic characteristics.

As another example, as the processing unit receives the audio input, the processing unit may record the digitized audio itself, or a representation of the digitized audio, in correspondence with indications of whether the hearing prosthesis is in the stimulation-on mode or is rather in the stimulation off mode, with or without determining one or more linguistic characteristics in the audio input. For instance, using an internal or real-world clock, the processing unit may timestamp the digitized audio (e.g., with periodic timestamps) and may correspondingly record times when the prosthesis transitions between stimulation-on mode to stimulation-off mode, and the combination of those two sets of data would thus indicate which portions of the audio input were received by the prosthesis when the prosthesis was in the stimulation-on mode and which portions of the audio input were received by the prosthesis when the prosthesis was in the stimulation-off mode. And the processing unit may output this data as well, again possibly in real-time as the processing unit establishes this data.

As still another example, in regular operation, the processing unit may be configured to record assorted other data related to operation of the hearing prosthesis, again in correspondence with indications of when the prosthesis is in the stimulation-on mode and when the prosthesis is in the stimulation-off mode.

For instance, the processing unit may record instances of the prosthesis receiving certain control signals from the user interface system 24, such as instances of user input changing various programs or other operational parameters of the prosthesis, and the processing unit may correlate those recorded instances with indications of the stimulation mode. Likewise, the processing unit may record various signal processing parameters of the processing unit, such as parameters of one or more classifier algorithms used to determine linguistic characteristics and/or parameters used by the translation module 18 to generate stimulation signals based on the received audio input.

As with the linguistic characteristics, the processing unit may keep track of such operational parameters and changes in operational parameters at times when the prosthesis is in the stimulation-on mode and may separately keep track of such operational parameters and changes in operational parameters at times when the prosthesis is in the stimulation-off mode. Furthermore, the processing unit may additionally include with this data various determined linguistic characteristics as discussed above. And here again, the processing unit may output this data, possibly in real-time as the processing unit establishes the data.

In practice, the processing unit may provide this and other data to the user interface system 24 in various forms for presentation to a user such as the recipient or a clinician. For example, the processing unit may provide the data in raw form, as one or more lists of metrics and associated values, such as a list of metrics corresponding with stimulation-on mode and a separate list of metrics corresponding with stimulation-off mode. As another example, the processing unit may structure the data as graphs and other charts more readily understandable at quick glance. For instance, rather than or in addition to listing the number of words spoken by the recipient on each of various days, the processing unit may provide a graph that shows change in number of words spoke per day or per other unit of time, which could then be analyzed in terms of the recipient's environment. In practice, the processing unit may generate these graphs as graphical user interfaces suitable for presentation by display 26.

In an alternative arrangement, note also that some of this analysis and presentation could be done by an external processing unit, such as processing unit 30 of an external computing device. In line with the discussion above, for instance, the processing unit 16 of the hearing prosthesis may record separate sets of linguistic characteristics corresponding with stimulation-on mode and stimulation-off mode, and processing unit 16 may periodically or otherwise from time to time provide the latest such sets of data to the processing unit 30 of the external computing device. Upon receipt of such data, processing unit 30 may then timestamp each received set of data with an indication of the current day, time of day, or the like. And processing unit 30 of the external computing device may then analyze the data to determine one or more linguistic characteristics in the audio, again possibly in correspondence with the stimulation mode of the prosthesis, and may similarly present output representing that information, such a depictions of changes in linguistic characteristics in the recipient's audio environment over time.

Figure 2:
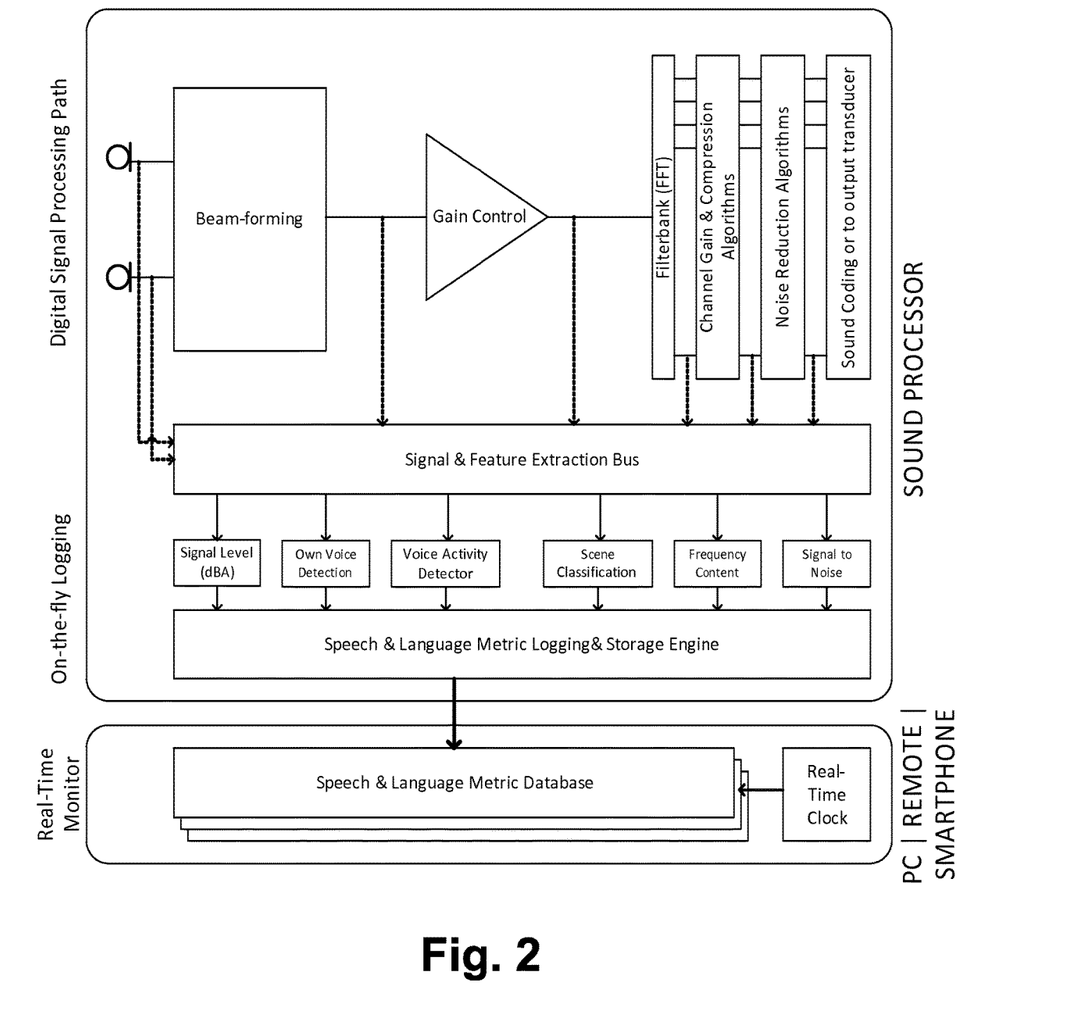
FIG. 2 is a block diagram depicting components of an example system.

FIG. 2 is next a block diagram depicting more specifically various components that may be included in a representative processing unit 16 and user interface system 24 in accordance with the present disclosure. In particular, FIG. 2 depicts processing unit 16 as a sound processor and user interface system 24 as a real-time monitor, such as a PC, smartphone, and/or remote control. The figure depicts on the sound processor a representative signal processing path for core hearing therapy. Further, the figure depicts extraction of certain metrics from various signal processing blocks, and forwarding of those metrics to a logging engine. The logging engine may then function to categorize the metrics, establish linguistic characterizations, and log the characterizations such as by incrementing counts of particular linguistic characterizations (e.g., number of words spoken by the recipient, number of words spoken by others, etc.), in correspondence with stimulation mode as discussed above. And the real-time monitor is then connected to the sound processor so as to read the stored logs, such as by periodically polling for the latest logged data. And the auxiliary device may timestamp and that data for comparison and trending, such as to determine and present indications of changes over time (e.g., one week versus the last, one month versus the last, etc.) in linguistic characteristics in the recipient's environment.

Figure 3:
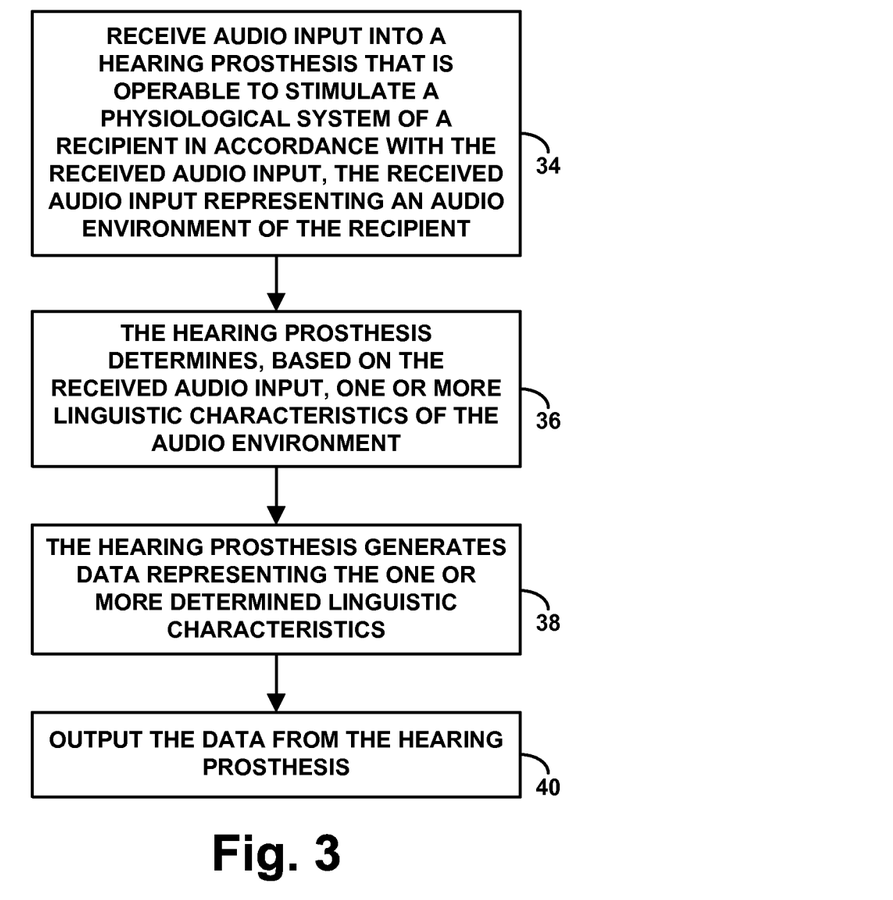
FIGS. 3-5 are flow charts depicting functions that can be carried out in accordance with representative methods.

FIG. 3 is next a flow chart depicting functions that can be carried out in accordance with a representative method. As shown in FIG. 3, at block 34, the method includes receiving audio input into the hearing prosthesis 12 that is operable to stimulate a physiological system of a recipient in accordance with the received audio input, the received audio input representing an audio environment of the recipient. Further, at block 36, the method involves the hearing prosthesis determining, based on the received audio input, one or more linguistic characteristics of the audio environment. Still further, at block 38, the method involves the hearing prosthesis generating data representing the one or more determined linguistic characteristics. And at block 40, the method involves outputting the data from the hearing prosthesis, such as providing the data to a computing system for presentation.

Although these functions are shown in series in the flow chart, the hearing prosthesis may in practice continuously carry out these functions in real-time. For instance, as the hearing prosthesis receives audio input, the hearing prosthesis may continuously or periodically analyze the audio input to determine linguistic characteristics and may continuously or periodically generate and output data representing the latest determined linguistic characteristics.

In line with the discussion above, the hearing prosthesis may be a hearing aid worn by the recipient or a device at least partially implanted in the recipient, and the act of stimulating the physiological system of the recipient may accordingly take various forms. For example, the hearing prosthesis could be a hearing aid, in which case the act of stimulating the physiological system of the recipient may involve delivering into an ear of the recipient an amplification of the received audio input. Alternatively, the hearing prosthesis could be a partially or fully implanted cochlear implant, in which case the act of stimulating the physiological system of the recipient may involve stimulating one or more cochlear electrodes of the recipient in accordance with the received audio input. And still alternatively, the hearing prosthesis could be a vibrationally-coupled hearing prosthesis, in which case the act of stimulating the physiological system of the recipient may involve delivering vibrations to the recipient in accordance with the received audio input. Other examples are possible as well.

Further, in line with the discussion above, the hearing prosthesis may have a stimulation mode that switches between a stimulation-on mode in which the hearing prosthesis is set to stimulate the physiological system of the recipient in accordance with the received audio input and a stimulation-off mode in which the hearing prosthesis is set to not stimulate the physiological system of the recipient in accordance with the received audio input. And in that case, the hearing prosthesis may take the stimulation mode into account while generating the data representing the determined one or more linguistic characteristics.

For example, the hearing prosthesis may include in the data indicia of when the hearing prosthesis was in the stimulation-on mode and/or when the hearing prosthesis was in the stimulation-mode. More particularly, the hearing prosthesis may include in the data one or more correlations between times when the hearing prosthesis was in the stimulation-on mode and one or more of the one or more determined linguistic characteristics, and perhaps similarly for times when the hearing prosthesis was in the stimulation-off mode. Similarly, the hearing prosthesis may maintain separate sets of data for each stimulation mode. For instance, separately for stimulation-on mode and stimulation-off mode, the hearing prosthesis may maintain counters or other rolled up indications of various determined linguistic characteristics, and the hearing prosthesis may increment or otherwise adjust those indications of determined linguistic metrics. The hearing prosthesis may then output those separate sets of data to facilitate separate analysis linguistic characteristics present in the recipient's environment during times of the prosthesis being in stimulation-on mode and linguistic characteristics present in the recipient's environment during times of the prosthesis being in stimulation-off mode.

As another example, using an internal clock or a real-world clock, the hearing prosthesis may time-stamp the received audio input and may record times when the hearing prosthesis was in the stimulation-on mode and times when the hearing prosthesis was in the stimulation-off mode. And the hearing prosthesis may correlate the recorded times with the timestamped received audio input so as to determine which audio input was received during stimulation-on mode and which audio input was received during stimulation-off mode. With that information, the hearing prosthesis may then provide output correlating certain determined linguistic characteristics with stimulation-on mode and other determined linguistic characteristics with stimulation-off mode.

Alternatively or additionally, the hearing prosthesis may determine the one or more linguistic characteristics specifically based on the audio input received during stimulation-on mode and not based on audio input received during stimulation-off mode. Further, whether or not the hearing prosthesis determines one or more linguistic characteristics based on the audio input received during stimulation-off mode, the hearing prosthesis could be arranged to limit the generated data to be based on just the audio input received during stimulation-on mode.

In practice as discussed above, the one or more linguistic characteristics may include a quantity of speech, such as a measure of quantity of speech by the recipient and a measure of quantity of speech by one or more people other than the recipient. Further, the one or more linguistic characteristics may comprise any of those noted above or other characteristics that are specifically related to language production and/or language receipt. And any or all of the determined linguistic characteristics may include a measure that is an estimate.

Still further, as discussed above, the act of receiving the audio input may involve receiving the audio input concurrently from multiple microphones. And in that case, the hearing prosthesis may determine based at least in part on the audio input received by the multiple microphones whether the audio input represents speech by the recipient or rather represents speech by a person other than the recipient.

In line with the discussion above, the data output by the hearing prosthesis in this method may be used to develop speech training for the recipient. For instance, given data indicating that the recipient is being exposed to a certain extent of speech (including speech production, speech reception, conversations, and so forth), a clinician may arrange for the recipient to be exposed to more speech, or to speech of different types, in an effort to help rehabilitate the recipient. Further, for recipients who are initially developing their speech skills (such as infants or the like), a clinician could use this output data to help identify speech errors, such as phoneme substitution for instance, and to develop appropriate therapy and further speech training.

Figure 4:
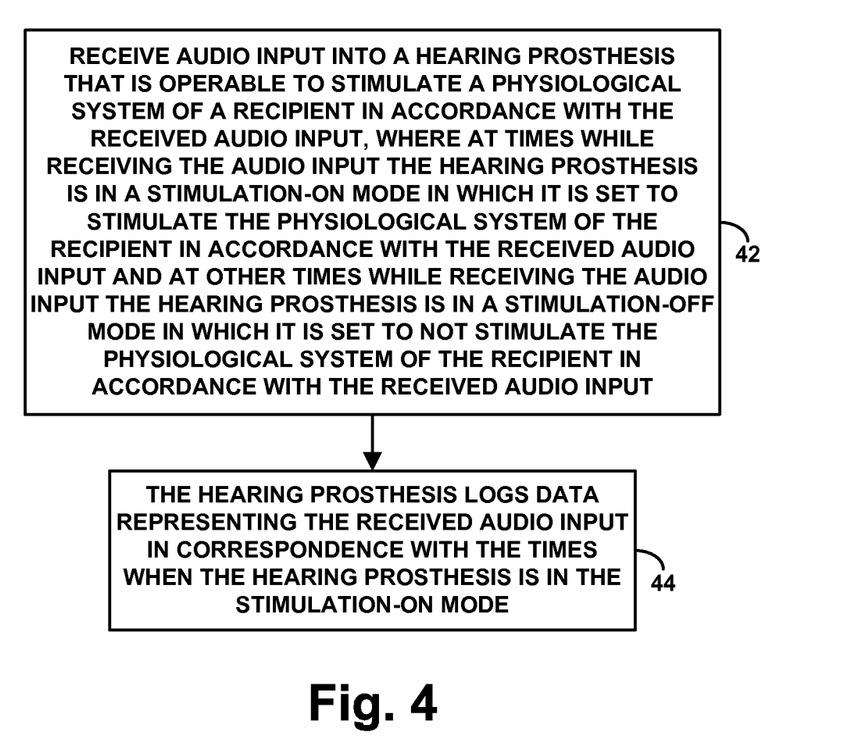

FIG. 4 is next another flow chart depicting functions that can be carried out in accordance with a representative method. As shown in FIG. 4, at block 42, the method involves receiving audio input into a hearing prosthesis that is operable to stimulate a physiological system of a recipient in accordance with the received audio input, where at times while receiving the audio input the hearing prosthesis is in a stimulation-on mode in which it is set to stimulate the physiological system of the recipient in accordance with the received audio input and at other times while receiving the audio input the hearing prosthesis is in a stimulation-off mode in which it is set to not stimulate the physiological system of the recipient in accordance with the received audio input. Further, at block 44, the method involves the hearing prosthesis logging data representing the received audio input in correspondence with the times when the hearing prosthesis is in the stimulation-on mode, such as recording in or in correlation with the logged data indicia of when the hearing prosthesis is in the stimulation-on mode, and perhaps separately when the hearing prosthesis is in the stimulation-off mode, or by maintaining counters separately for the two stimulation modes.

Figure 5:
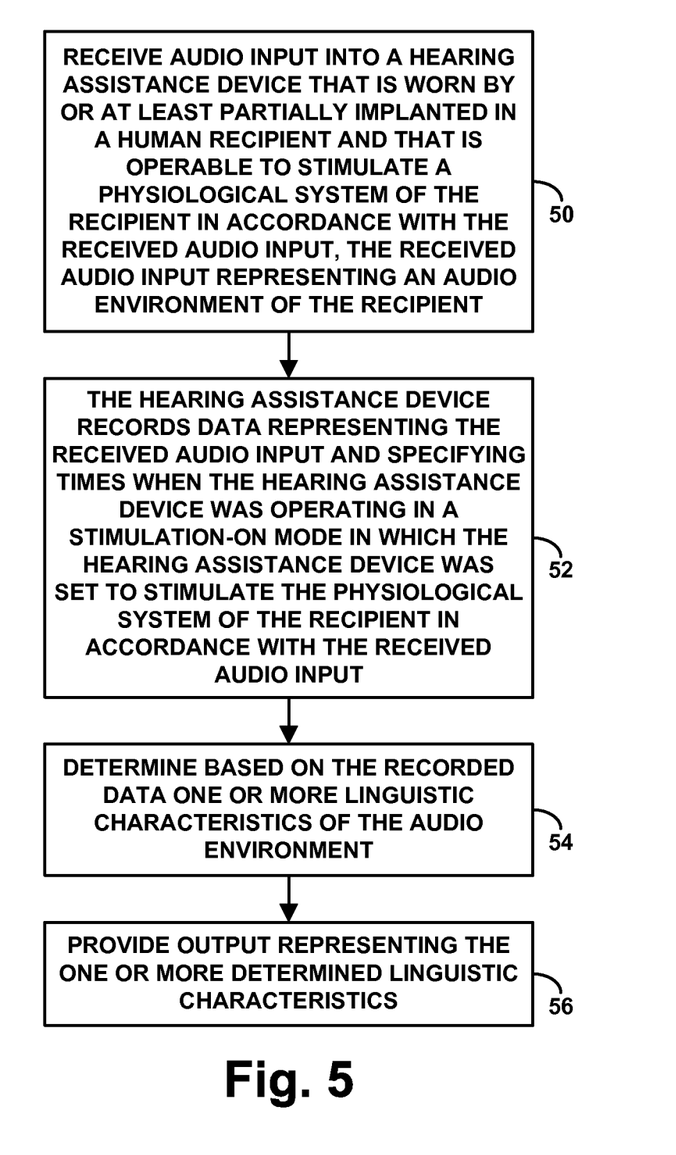

FIG. 5 is next yet another flow chart depicting functions that can be carried out in accordance with a representative method. As shown in FIG. 5, at block 50, the method involves receiving audio input into a hearing assistance device that is worn by or at least partially implanted in a human recipient and that is operable to stimulate a physiological system of the recipient in accordance with the received audio input, the received audio input representing an audio environment of the recipient. Further, at block 52, the method involves the hearing assistance device recording data representing the received audio input and specifying times when the hearing assistance device was operating in a stimulation-on mode in which the hearing assistance device was set to stimulate the physiological system of the recipient in accordance with the received audio input. Still further, at block 54, the method involves determining based on the recorded data one or more linguistic characteristics of the audio environment. And at block 56, the method involves providing output representing the one or more determined linguistic characteristics.

In practice, as discussed above, the hearing assistance device itself may carry out the acts of determining the one or more linguistic characteristics and providing the output representing the one or more determined linguistic characteristics. Alternatively, a processing system external to the hearing assistance device, such as a separate computing device for instance, may carry out those functions, in which case the method may further include transferring the data from the hearing assistance device to the external processing system. In either case, as further discussed above, the output may also associate the one or more determined linguistic characteristics with the specified times when the audio input caused the hearing assistance device to stimulate the physiological system of the recipient.

Exemplary embodiments have been described above. It should be understood, however, that numerous variations from the embodiments discussed are possible, while remaining within the scope of the invention.

What is claimed is:

1. A hearing prosthesis, comprising:
   one or more microphones configured to receive audio inputs representing an audio environment of the hearing prosthesis, wherein the hearing prosthesis is configured to selectively stimulate a physiological system of a recipient in accordance with one or more of the audio inputs;
   one or more stimulus outputs;
   a processing unit configured to:
      determine, based on the audio inputs, one or more linguistic characteristics of the audio environment,
      generate data representing the one or more linguistic characteristics; and
      output the data from the hearing prosthesis.

2. The hearing prosthesis of claim 1, wherein the one or more linguistic characteristics comprise a measure of speech produced by the recipient.

3. The hearing prosthesis of claim 2, wherein the measure of speech produced by the recipient comprises a measure of quantity of speech by the recipient.

4. The hearing prosthesis of claim 2, wherein the measure of speech produced by the recipient comprises at least one characteristic selected from the group consisting of:
   a measure of proportion of time spent by the recipient speaking,
   a measure of quantity of conversational turns by the recipient,
   a measure of quantity of conversations initiated by the recipient,
   a measure of quantity of phonetic features produced by the recipient, and
   a measure of length of utterances by the recipient.

5. The hearing prosthesis of claim 1, wherein the one or more linguistic characteristics comprise a measure of speech produced by one or more people other than the recipient.

6. The hearing prosthesis of claim 5, wherein the measure of speech produced by one or more people other than the recipient comprises a measure of quantity of speech produced by the one or more people other than the recipient.

7. The hearing prosthesis of claim 1, wherein the one or more linguistic characteristics comprise a measure of quantity of speech interaction between the recipient and one or more people other than the recipient.

8. The hearing prosthesis of claim 1, wherein the one or more linguistic characteristics comprise a measure of speech quality.

9. The hearing prosthesis of claim 1, wherein the linguistic characteristics comprise (i) a measure of quantity of speech by the recipient and (ii) a measure of quantity of speech by one or more people other than the recipient.

10. The hearing prosthesis of claim 1, wherein the hearing prosthesis is configured to selectively operate in a stimulation-on mode in which the processing unit is configured to convert the audio inputs into stimulation signals for delivery to the physiological system of the recipient via the one or more stimulus outputs and a stimulation-off mode in which the processing unit does not convert the audio inputs into stimulation signals.

11. The hearing prosthesis of claim 10, wherein the processing unit only generates the data representing the one or more linguistic characteristics when the hearing prosthesis is in the stimulation-on mode.

12. The hearing prosthesis of claim 10, wherein to generate data representing the one or more determined linguistic characteristics, the processing unit is configured to:
   log the one or more linguistic characteristics separately for (i) when the hearing prosthesis is in the stimulation-on mode and (ii) when the hearing prosthesis is in the stimulation-off mode.

13. The hearing prosthesis of claim 12, wherein the data output by the hearing prosthesis associates the one or more linguistic characteristics with specified times when the hearing prosthesis was operating in the stimulation-on mode.

14. The hearing prosthesis of claim 10, wherein to output the data from the hearing prosthesis, the processing unit is configured to:
   output separate sets of data (i) corresponding with when the hearing prosthesis was in the stimulation-on mode and (ii) corresponding with when the hearing prosthesis was in the stimulation-off mode.

15. The hearing prosthesis of claim 10, wherein the hearing prosthesis is switchable between the stimulation-on mode and the stimulation-off mode by the recipient.

16. The hearing prosthesis of claim 1, wherein the hearing prosthesis comprises a hearing aid and wherein the one or more stimulus outputs comprise a receiver configured to output an amplified acoustic signal.

17. The hearing prosthesis of claim 1, wherein the hearing prosthesis comprises a cochlear implant, and wherein the one or more stimulus outputs comprise one or more cochlear electrodes configured to deliver electrical stimulation signals to the recipient.

18. The hearing prosthesis of claim 1, wherein the hearing prosthesis comprises a vibrationally-coupled hearing prosthesis configured to deliver vibrations to the recipient in accordance with the audio inputs.

19. The hearing prosthesis of claim 1, wherein the processing unit is configured to:

determine the one or more linguistic characteristics of the audio environment, generate the data representing the one or more linguistic characteristics, and output the data in real-time as the hearing prosthesis receives the audio input.

20. The hearing prosthesis of claim 1, wherein the processing unit is configured to output the data from the hearing prosthesis to a computing system for presentation to a user.

21. The hearing prosthesis of claim 1, wherein the hearing prosthesis receives a plurality of audio inputs, and wherein the processing unit is configured to:
- record times when one or more of the plurality of audio inputs causes the hearing prosthesis to stimulate the physiological system of the recipient;
- use the recorded times to determine a selected one or more of the plurality of audio inputs that caused the hearing prosthesis to stimulate a physiological system of the recipient; and
- determine the linguistic characteristics based only the one or more of the plurality of audio inputs.

22. The hearing prosthesis of claim 1, further comprising:
- a plurality of microphones configured to receive the audio inputs, and wherein the processing unit is configured to:
- determine based at least in part on audio inputs received by the plurality of microphones whether the audio inputs represent speech by the recipient or rather represent speech by a person other than the recipient.

\* \* \* \* \*